United States Patent [19]

Tokunaga et al.

[11] Patent Number: 4,742,063
[45] Date of Patent: May 3, 1988

[54] AGRICULTURAL-HORTICULTURAL FUNGICIDE EMPLOYING 5H-1,3,4-THIADIAZOLO[3,2-A]PYRIMIDIN-5-ONE DERIVATIVES

[75] Inventors: Yukio Tokunaga, Shizuoka; Yoshiyuki Kojima, Kakegawa; Shinichiro Maeno; Nobumitsu Sawai, both of Shizuoka; Yasuo Saso, Miyagi, all of Japan

[73] Assignees: Kumiai Chemical Industry Co., Ltd.; Ihara Chemical Industry Co., Ltd., both of Tokyo, Japan

[21] Appl. No.: 27,252

[22] Filed: Mar. 18, 1987

[30] Foreign Application Priority Data

Mar. 19, 1986 [JP] Japan .................................. 61-61746

[51] Int. Cl.$^4$ ............................................. A01N 43/54
[52] U.S. Cl. .................................................... 514/258
[58] Field of Search ......................................... 514/258

[56] References Cited

FOREIGN PATENT DOCUMENTS 52-118494 10/1977 Japan .

Primary Examiner—Allen J. Robinson
Attorney, Agent, or Firm—Oblon, Fisher, Spivak, McClelland & Maier

[57] ABSTRACT

It is disclosed that a class of 5H-1,3,4-thiadiazolo[3,2-a]pyrimidin-5-one derivatives exhibit remarkable fungicidal activities for cucumber gray mold, cucumber downy mildew, Alternaria sooty spot of Chinese mustard, rice blast, etc.

19 Claims, No Drawings

AGRICULTURAL-HORTICULTURAL FUNGICIDE EMPLOYING 5H-1,3,4-THIADIAZOLO[3,2-A]PYRIMIDIN-5-ONE DERIVATIVES

FIELD OF THE INVENTION

This invention relates to a novel agricultural-horticultural fungicide. More particularly, this invention relates to an agricultural-horticultural fungicide composition comprising a 5H-1,3,4-thiadiazolo[3,2-a]pyrimidin-5-one derivative and an agricultural-horticulturally acceptable carrier.

BACKGROUND OF THE INVENTION

In the specification of Japanese Laying-Open Patent Publication No. 52-118494 (1977), compounds represented by the general formula

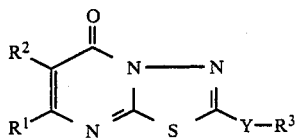

wherein $R^1$ is an alkyl group or an aryl group; $R^2$ is a hydrogen atom, a halogen atom, a nitro group, a carboalkoxy group or an alkyl group; $R^3$ is an alkyl group or an aralkyl group and Y is a —SO— or —SO$_2$— group, are disclosed and it is described that these compounds exhibit an activity inhibiting proliferation of cancer cells and are effective as anticancer agents. Also it is described that these compounds are useful agricultural chemicals such as herbicides or as intermediates for synthesizing pharmaceuticals. However, it has not been known that these compounds can be used for control of plant diseases.

We carried out an intensive study in search of compounds which are useful as fungicides and effective for control of phathogenic fungi or genus Alternaria among derivatives of 5H-1,3,4-thiadiazolo[3,2-a]pyrimidin-5-one and we have found that a specific class of 5H-1,3,4-thiadiazolo[3,2-a]pyrimidin-5-one derivatives have a fungicidal activity against Alternaria sooty spot of Chinese mustard (*Brassica Rapa* var. pervidis) caused by *Alternaria brassicicola*, apple Alternaria leaf spot caused by *Alternaria mali*, pear black spot caused by *Alternaria kikuchiana*, etc. far better than "Captan", copper 8-oxyquinolinate, "Propineb", etc. which have been used for the control of these diseases.

DISCLOSURE OF THE INVENTION

The agricultural-horticultural fungicide composition of the present invention contains a 5H-1,3,4-thiadiazolo[3,2-a]pyrimidin-5-one derivative represented by the general formula (I)

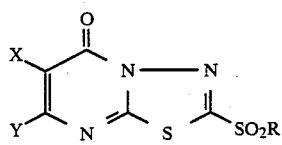

(I)

wherein X is a hydrogen atom, a halogen atom, a lower alkyl group or a lower alkoxycarbonyl group, Y is a hydrogen atom, a lower alkyl group or a phenyl group; R is a linear or branched alkyl group, a benzyl group, a mono- or dimethylbenzyl group or a phenethyl group, with a proviso that when Y is a hydrogen atom, or R is a mono- or dimethylbenzyl group, X is a lower alkoxycarbonyl group.

Specific examples of the compounds of the general formula are listed in Table 1.

TABLE 1

| Compound No. | X | Y | R | m.p. (°C.) |
|---|---|---|---|---|
| 1 | H | CH$_3$ | CH$_3$ | 185~188 |
| 2 | " | " | C$_2$H$_5$ | 170~175 |
| 3 | " | " | i-C$_3$H$_7$ | 153~154 |
| 4 | " | " | n-C$_4$H$_9$ | 131~132 |
| 5 | " | " | t-C$_4$H$_9$ | 154~161 |
| 6 | " | " | n-C$_5$H$_{11}$ | 153~154 |
| 7 | " | " | i-C$_5$H$_{11}$ | 129~132 |
| 8 | " | " | sec-C$_5$H$_{11}$ | 72~73 |
| 9 | " | " | n-C$_6$H$_{13}$ | 111~115 |
| 10 | " | " | n-C$_7$H$_{15}$ | 135~137 |
| 11 | " | " | n-C$_8$H$_{17}$ | 117~118 |
| 12 | " | " | n-C$_{12}$H$_{25}$ | 109~116 |
| 13 | " | " | CH$_2$—C$_6$H$_5$ | 173~175 |
| 14 | " | " | CH$_2$CH$_2$—C$_6$H$_5$ | 133~135 |
| 15 | Cl | " | CH$_2$—C$_6$H$_5$ | 225~230 |
| 16 | CH$_3$ | " | " | 169~173 |
| 17 | CO$_2$C$_2$H$_5$ | " | " | 141~145 |
| 18 | " | H | " | 200~203 |
| 19 | " | " | n-C$_8$H$_{17}$ | 99~103 |
| 20 | H | C$_2$H$_5$ | CH$_2$—C$_6$H$_5$ | 195~197 |
| 21 | " | i-C$_3$H$_7$ | " | 165~167 |
| 22 | " | t-C$_4$H$_9$ | " | 180~185 |
| 23 | CO$_2$C$_2$H$_5$ | H | n-C$_6$H$_{13}$ | 120~122 |
| 24 | H | n-C$_3$H$_7$ | CH$_2$—C$_6$H$_5$ | 158~160 |
| 25 | " | " | n-C$_6$H$_{13}$ | 101~103 |
| 26 | " | t-C$_4$H$_9$ | " | 87~90 |
| 27 | CH$_3$ | CH$_3$ | " | 102~103 |
| 28 | Cl | " | n-C$_4$H$_9$ | 135~136 |
| 29 | " | " | n-C$_6$H$_{13}$ | 122~124 |
| 30 | H | C$_6$H$_5$ | CH$_2$—C$_6$H$_5$ | 249~251 |
| 31 | " | " | n-C$_4$H$_9$ | 153~155 |
| 32 | " | " | n-C$_6$H$_{13}$ | 131~134 |
| 33 | Cl | CH$_3$ | n-C$_5$H$_{11}$ | 136~141 |
| 34 | CO$_2$CH$_3$ | H | n-C$_6$H$_{13}$ | 95~97 |
| 35 | " | " | CH$_2$—C$_6$H$_4$—CH$_3$ | 181~185 |
| 36 | Cl | CH$_3$ | i-C$_5$H$_{11}$ | 145~150 |
| 37 | F | " | n-C$_6$H$_{13}$ | 107~108.5 |

TABLE 1-continued

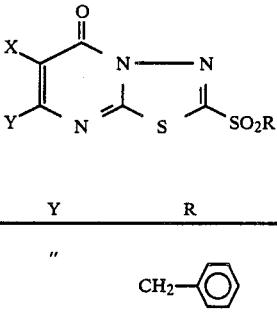

| Compound No. | X | Y | R | m.p. (°C.) |
|---|---|---|---|---|
| 38 | " | " | CH₂—⌬ | 226.5~227.5 |
| 39 | CO₂C₂H₅ | H | CH₂—⌬—CH₃ | 162~167 |
| 40 | H | CH₃ | CH₂CHC₄H₉—n<br>\|<br>C₂H₅ | 73~75 |
| 41 | F | " | n-C₇H₁₅ | 107~108 |
| 42 | H | C₂H₅ | n-C₆H₁₃ | |
| 43 | CO₂CH₃ | H | n-C₇H₁₅ | |
| 44 | " | " | CH₃<br>CH₂—⌬—CH₃ | |
| 45 | " | " | CH₂—⌬(CH₃)(CH₃) | |

Of these compounds, preferred are those wherein R is a $C_{1-12}$-alkyl, especially $C_{4-8}$-alkyl group, those wherein X is a hydrogen atom or a halogen atom and Y is a lower alkyl group, and those wherein X is a hydrogen atom or a chlorine atom, Y is a lower alkyl group and R is a $C_{4-8}$-alkyl group.

The 5H-1,3,4-thiadiazolo[3,2-a]pyrimidin-5-one derivatives used as the active ingredient in the fungicide of the present invention are known and can be easily prepared by the process described in Japanese Laying-Open Patent Publication No. 52-118494 (1977), that is, by oxidizing a compound represented by the general formula (II)

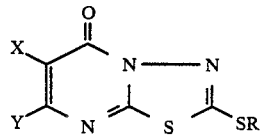 (II)

wherein X, Y and R are as defined above.

The oxidation of compounds of the general formula (II) can be carried out by a method usually employed for oxidation of organic sulfides.

Examples of the employable oxidizing reagents are hydrogen peroxide, an organic peracid such as m-chloroperbenzoic acid, an inorganic peroxide such as OXONE® (a tradename of DuPont Company, containing potassium hydrogen peroxosulfate), etc.

Examples of the solvent employable for the oxidation reaction are water; halogenated hydrocarbons such as dichloromethane, chloroform, etc.; fatty acids such as acetic acid, propionic acid, etc.; ketones such as acetone, methylethyl ketone, etc.; amides such as dimethylformamide, dimethyl acetamide; etc.; alcohols such as methyl alcohol; ethyl alcohol, etc. When water is used, it is preferred that a compound of the general formula (II) is first dissolved in a water-miscible organic solvent and then mixed with water.

The oxidation can be carried out at a temperature between −20° C. and the boiling temperature of the used solvent.

The amount of the oxidizing reagent to be used is usually twice the equivalent amount of the compound of the general formula (II), but there is no strict restriction.

Compounds of the general formula (II) used as the starting material are known per se, and can be prepared by known methods, for instance processes described in Agr. Biol. Chem. 37(5) 1197–1201 and Japanese Laying-Open Patent Publication No. 58-177997 (1983). That is, compounds of the general formula (II) can be prepared by reacting a compound of the general formula (III)

 (III)

wherein R is as defined above, with a compound of the general formula (IV)

 (IV)

wherein X and Y are as defined above, and $R^2$ is a lower alkyl group or a compound of the general formula (V)

 (V)

$$R^2OCH=C(CO_2R^2)_2$$

wherein $R^2$ is a lower alkyl group, in a high boiling solvent or in the presence of a condensing agent such as polyphosphoric acid.

Compounds of the general formulas (III), (IV) and (V) are known, or otherwise can be prepared by conventional methods. Many of them are commercially available products.

SPECIFIC DESCRIPTION OF EMBODIMENTS

The specific preparation processes are illustrated by way of working examples.

Preparation Example 1-a

Preparation of 2-hexylthio-7-methyl-5H-1,3,4-thiadiazolo[3,2-a]pyrimidin-5-one

In 24 ml of water and 24 ml of ethanol, 11.6 g of 2-amino-5-mercapto-1,3,4-thiadiazole and 3.8 g of sodium hydroxide were dissolved, 14.0 g of 1-bromohexane was added to this solution, and the mixture was heated to 70°–80° C. and stirred for 3 hours. After cooling, water was added and the mixture was filtered. The residue was washed with water, dried under reduced pressure, and recrystallized from an ethanol/n-hexane (1:1) mixture. Thus 14.5 g of 2-amino-5-hexylthio-1,3,4-thiadiazole was obtained. m.p. 113°–115° C. Yield 77%.

Seven (7.0) grams of the thus obtained 2-amino-5-hexylthio-1,3,4-thiadiazole and 4.3 g of ethyl acetoacetate were mixed with 8 g of polyphosphoric acid, and the mixture was heated to 130°–150° C. and stirred for 30 minutes. After cooling, water was added to the reaction mixture, and the resulting mixture was extracted with chloroform. The organic layer was washed with a sodium hydrogen carbonate aqueous solution and water respectively, dried over anhydrous sodium sulfate. The solvent was distilled off. The residue was purified by developing on a silica gel column, and eluting with an ethylacetate/n-hexane (1:1) mixture, and thus 7.5 g of 2-hexylthio-7-methyl-5H-1,3,4-thiadiazolo[3,2-a]pyrimidin-5-one was obtained. Refraction index $n_D^{20}$: 1.6003. Yield 82%.

Preparation Example 1-b

Preparation of 2-hexanesulfonyl-7-methyl-5H-1,3,4-thiadiazolo[3,2-a]pyrimidin-5-one A mixture of 6.1 g of 2-hexylthio-7-methyl-5H-1,3,4-thiadiazolo[3,2-a]pyrimidin-5-one, 9.1 g of a 30% hydrogen peroxide solution and 14 ml of acetic acid was heated to 65°–75° C. and stirred for 2 hours and 15 minutes. After cooling, water was added to the mixture and the resulting mixture was extracted with chloroform. The organic layer was washed with a sodium thiosulfate and water respectively, and dried over anhydrous sodium sulfate anhydrate. The solvent was distilled off. The residue was recrystallized from ethanol and thus 3.2 g of 2-hexanesulfonyl-7-methyl-5H-1,3,4-thiadiazolo[3,2-a]pyrimidin-5-one was obtained. m.p. 111°–115° C. Yield 45%.

Preparation Example 2-a

Preparation of 2-benzylthio-6-ethoxycarbonyl-5H-1,3,4-thiadiazolo[3,2-a]pyrimidin-5-one Thirteen point four (13.4) grams of 2-amino-5-benzylthio-1,3,4-thiadiazole, which was prepared by the same procedure as in Preparation 1-a, 14.0 g of diethyl ethoxymethylenemalonate and 24 g of polyphosphoric acid were mixed, and the mixture was stirred at 130°–150° C. for 15 minutes. After cooling, water was added to the reaction mixture and the resulting mixture was extracted with chloroform. The organic layer was washed with a sodium hydrogen carbonate aqueous solution and water respectively and dried over anhydrous sodium sulfate. The solvent was distilled off, the residue was recrystallized from ethanol, and thus 9.4 g of 2-benzylthio-6-ethoxycarbonyl-5H-1,3,4-thiadiazolo[3,2-a]pyrimidin-5-one was obtained. m.p. 129°–132° C. Yield 45%.

Preparation Example 2-b

Preparation of 2-benzylsulfonyl-6-ethoxycarbonyl-5H-1,3,4-thiadiazolo[3,2-a]pyrimidin-5-one In 240 ml of methanol, 6.3 g of 2-benzylthio-6-ethoxycarbonyl-5H-1,3,4-thiadiazolo[3,2-a]pyrimidin-5-one was dissolved. A suspension of 27.7 g of OXONE ® dispersed in 110 ml of water was added to the methanol solution. The mixture was stirred at 60° C. for 2 hours, and was extracted with chloroform after cooling. The organic layer was washed with a sodium thiosulfate solution and water respectively and dried over anhydrous sodium sulfate. The solvent was distilled off. The residue was recrystallized from an acetonitrile/isopropylether (2:1) mixture and 3.3 g of 2-benzylsulfonyl-6-ethoxycarbonyl-5H-1,3,4-thiadiazolo[3,2-a]pyrimidin-5-one was obtained. m.p. 200°–203° C. Yield 49%.

Preparation Example 3-a

Preparation of 2-hexylthio-7-phenyl-5H-1,3,4-thiadiazolo[3,2-a]pyrimidin-5-one

To 190 ml of ethanol and 240 ml of water, 81.5 g of 2-amino-5-mercapto-1,3,4-thiadiazole and 26.9 g of sodium hydroxide were added. To this mixture 99.0 g of 1-bromohexane was added and the resulting mixture was stirred at 60°–70° C. for 2 hours. After cooling, water was added to the mixture and the mixture was filtered. The residue was washed with water, dried under reduced pressure, and recrystallized from an ethanol/hexane mixture. Thus 100.5 g of 2-amino-5-hexylthio-1,3,4-thiadiazole was obtained. m.p. 113°–115° C. Yield 77%.

Three point seven (3.7) grams of 2-amino-5-hexylthio-1,3,4-thiadiazole, 3.4 g of ethyl benzoylacetate and 5 g of polyphosphoric acid were mixed and stirred at 130°–140° C. for 30 minutes. After cooling, chloroform and water were added to the mixture and extraction was carried out. The organic layer was washed with a sodium hydrogen carbonate aqueous solution and water respectively and dried over anhydrous sodium sulfate. The solvent was distilled off and thus 5.5 g of 2-hexylthio-7-phenyl-5H-1,3,4-thiadiazolo[3,2-a]pyrimidin-5-one was obtained. Yield 99%. This substance was recrystallized from ethanol and the purified compound showed a m.p. of 90°–91° C.

Preparation Example 3-b

Preparation of 2-hexanesulfonyl-7-phenyl-5H-1,3,4-thiadiazolo[3,2-a]pyrimidin-5-one (Compound 32)

In 15 ml of acetic acid and 3 ml of water, 4.8 g of 2-hexylthio-7-phenyl-5H-1,3,4-thiadiazolo[3,2-a]pyrimidin-5-one was dissolved. To this solution, 0.23 g of sodium tungstate dihydrate and 11.0 g of 30% hydrogen peroxide solution were added, and the solution was stirred at 50°–60° C. for 30 minutes. After cooling, the solution was extracted with chloroform, the organic layer was washed with a sodium thiosulfate solution and water respectively. The solvent was distilled off, the residue was recrystallized from ethanol, and thus 2.5 g of 2-hexanesulfonyl-7-phenyl-5H-1,3,4-thiadiazolo[3,2-a]pyrimidin-5-one was obtained. m.p. 131°–134° C. Yield 50%.

As agricultural-horticultural fungicides, the compounds of the present invention per se can be used. But usually, the compounds are prepared into a formulation such as a dust formulation, wettable powder, emulsifiable concentrate, granular preparation, pellet preparation, etc. by mixing with an ordinary carrier, surfactant, dispersant or adjuvant by a conventional method.

Examples of the preferred carriers are: a solid carrier such as talc, bentonite, clay, kaolin, diatomaceous earth, white carbon, vermiculight, slaked lime, siliceous sand, ammonium sulfate, urea, etc. and a liquid carrier such as isopropyl alcohol, xylene, cyclohexanone, etc. As surfactants, alcohol sulfate ester salts, alkylaryl sulfonate ester salts, lignosulfonate salts, diarylmethanesulfonate salts, polyoxyethyleneglycol ethers, polyoxyethylenealkylaryl ethers, polyoxyethylenesorbitane monoalkylate, etc. can be used for instance. As adjuvants, carboxymethyl cellulose, polyethyleneglycol, gum arabic, etc. can be used for instance. The preparations are applied as they are or diluted with to a suitable concentration with a suitable diluent.

The concentration of the active ingredient can be varied according to circumstances. In the case of dust or granular preparations, 0.5–20% by weight is a suitable concentration and in the case of emulsion or water-dispersed preparations, 5–80% by weight is proper.

The application amount of the fungicide of the present invention varies depending upon species of the used compound, kind of disease, conditions of disease injury, degree of damage, environmental conditions, type of the employed preparation, etc. When dust or granular preparations are used, a suitable amount is selected from the range of 10–500 g active ingredient per ten ares. When the fungicide is used finally in a liquid form such as an emulsion or a water-dispersed preparation, a suitable concentration is selected from the range of 10–2000 ppm.

Now the fungicide compositions of the present invention will be illustrated by way of working examples. In the following formulation examples, percentage referred to is by weight.

Formulation Example 1 (dust preparation)

Two (2)% Compound 1, 5% diatomaceous earth and 93% clay were ground homogeneously and mixed to form a dust preparation.

Formulation Example 2 (water-dispersible preparation)

Fifty (50)% Compound 2, 45% diatomaceous earth, 2% sodium dinaphthylmethanesulfonate and 3% sodium lignosulfonate were ground and homogeneously mixed to form a water-dispersible preparation.

Formulation Example 3 (emulsion preparation)

Thirty (30)% Compound 11, 20% cyclohexanone, 11% polyoxyethylenealkylaryl ether, 4% calcium alkylbenzenesulfonate, and 35% methylnapththalene were homogeneously mixed and emulsified.

Formulation Example 4 (granular preparation)

Five (5)% Compound 4, 2% sodium salt of lauryl alcohol sulfate ester, 5% sodium lignosulfonate, 2% carboxymethyl cellulose and 86% clay were mixed and ground. To this mixture, 20% of water was added and kneaded. The kneaded mass was formed into 14–32 mesh granules by an extrusion granulating machine. The granules were dried.

The agricultural-horticultural fungicide of the present invention effectively controls Alternaria sooty spot (*Alternaria brassicicola*) of Chinese mustard (*Brassica Rapa* var. pervidis), apple Alternaria leaf spot (*Alternaria mali*), pear block spot (*Alternaria kikuchiana*), etc. as well as cucumber gray mold (*Botrytis cinerea*), cucumber downy mildew (*Pseudoperonospora cubensis*), rice blast (*Pyricularia oryzae*), etc.

This activity is exhibited both preventively and curatively, and that durably. Further, the fungicide of the present invention is characterized by having high safety for crop plants, homoiothermic animals as well as aquatic animals.

The effect of the fungicide of the present invention will now be illustrated by way of test examples.

Test Example 1

(Protective effect on sooty spot of Chinese mustard)

In 9 cm×9 cm plastic pots, each 12 seeds of Chinese mustard (*Brassica Rapa* var. pervidis) were sown and grown to the cotiledonous stage in a greenhouse for 7 days. To the seedlings a water-dispersible preparation prepared in accordance with Formulation Example 2 and diluted with water containing a suitable amount of a surfactant to an active ingredient concentration of 50 ppm or 500 ppm was sprayed at a rate of 10 ml per pot.

After air-dried, the seedlings were inoculated with an aqueous suspension of spores of the pathogen (*Alternaria brassicicola*) and kept in a moist chamber at 30° C. Three days after inoculation, number of lesions was counted, average numbers thereof per leaf were worked out, and the control activity was calculated as follows.

Control activity (%) =

$$\left(1 - \frac{\text{Average number of lesions in treated sections}}{\text{Average number of lesions in untreated sections}}\right) \times 100$$

The results are shown in Tables 2 and 3.

TABLE 2

| (50 ppm) | |
|---|---|
| Compound Tested | Control Activity (%) |
| 4 | 81.0 |
| 6 | 100 |
| 7 | 72.7 |
| 9 | 91.7 |
| 10 | 96.0 |
| 11 | 92.0 |
| 13 | 91.8 |
| 14 | 96.9 |
| 16 | 70.2 |
| 19 | 67.0 |
| 20 | 93.0 |
| 21 | 86.1 |
| Captan* | 51.0 |
| Untreated | 0 |

*[N—(trichloromethylthio)-4-cyclohexene-1,2-dicarboximide]

TABLE 3

| (500 ppm) | |
|---|---|
| Compound No. | Control Activity |
| 23 | 99.1 |
| 24 | 99.4 |
| 25 | 99.4 |
| 27 | 97.1 |
| 29 | 100.0 |
| 31 | 97.9 |
| 32 | 91.8 |
| 33 | 98.1 |
| 34 | 97.1 |
| 35 | 97.7 |
| 36 | 100.0 |
| 37 | 99.4 |
| 38 | 88.3 |
| 39 | 78.1 |

Test Example 2

(Control of apple Alternaria leaf spot)

Young twigs with 6–7 leaves detached from an apple tree (variety: Indo) were put in a glass cylinder. A water-dispersed fungicide prepared in accordance with Formulation Example 2 and diluted with water into an active ingredient concentration of 1500 ppm was sprayed on the twigs.

After air-dried, the plants were inoculated with spores of the pathogen (*Alternaria mali*) suspended in water and placed in a moist chamber at 28° C. Four days after the inoculation, the damage index as defined below was determined and control activity was calculated.

Damage Index (%) =

$$\frac{(n_1 \times 1) + (n_2 \times 2) + (n_3 \times 3) + (n_4 \times 4) + (n_5 \times 5)}{5N} \times 100$$

Wherein
N is the total number of the examined leaves
$n_1$ is the number of the affected leaves on which area of lesion is less than 5%
$n_2$ is the number of the affected leaves on which area of lesion is less than 5~10%
$n_3$ is the number of the affected leaves on which area of lesion is less than 11~25%
$n_4$ is the number of the affected leaves on which area of lesion is less than 26~50%
$n_5$ is the number of the affected leaves on which area of lesion is more than 50%

Control activity (%) =

$$\left(1 - \frac{\text{Damage index in treated sections}}{\text{Damage index in untreated sections}}\right) \times 100$$

The results are indicated in Table 4.

TABLE 4

| Compound Tested | Control Activity |
|---|---|
| 6 | 75.8 |
| 10 | 82.4 |
| 11 | 92.0 |

Test Example 3

(Preventive effect on cucumber gray mold)

In 9 cm×9 cm square plastic pots, each 12 seeds of cucumber (variety: "Sagami-hanjiro") were sown and the plants were grown in a greenhouse for seven days. Onto the seedlings which had cotyledons developed, a water-dispersible preparation prepared in accordance with Formulation Example 2 and diluted with water containing a suitable amount of a surfactant to an active ingredient concentration of 500 ppm was sprayed at a rate of 10 ml per pot. Four days after the inoculation, the index of affection as defined below was checked.

Index of Affection

0: No affection recognized
1: Area of the affected portion is less than 25%
2: Area of the affected portion is less than 26~50%
3: Area of the affected portion is less than 51~75%
4: Area of the affected portion is more than 75%

The results are indicated in Table 5.

TABLE 5

| Compound Tested | Index of Affection |
|---|---|
| 2 | 0 |
| 4 | 0 |
| 6 | 0 |
| 7 | 0 |
| 8 | 0 |
| 9 | 0 |
| 10 | 0 |
| 11 | 0 |
| 13 | 0 |
| 14 | 1 |
| 18 | 1 |
| 19 | 1 |
| 20 | 0 |
| 23 | 0 |
| 24 | 0 |
| 25 | 0 |
| 26 | 0 |
| 27 | 0 |
| 28 | 0 |
| 29 | 0 |
| 31 | 0 |
| 32 | 1 |
| 33 | 0 |
| 34 | 0 |
| 35 | 0 |
| 36 | 0 |
| 37 | 0 |
| 38 | 1 |
| 39 | 1 |
| untreated | 4 |

We claim:

1. A method of protecting plants against agricultural or horticultural fungi, which comprises applying to said plants a fungicidally effective amount of a 5H-1,3,4-thiadiazolo[3,2-a]pyrimidin-5-one derivative represented by the formula (I)

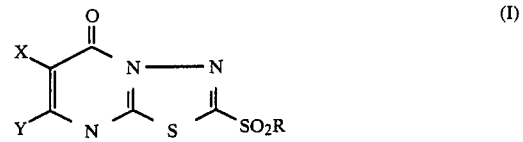

wherein
X is a hydrogen atom, a halogen atom, a lower alkyl group or a lower alkoxycarbonyl group;
Y is a hydrogen atom, a lower alkyl group or a phenyl group; and
R is a linear or branched $C_1$–$C_{12}$ alkyl group, a benzyl group, a mono- or dimethylbenzyl group or a phenethyl group;
with a proviso that when Y is a hydrogen atom or R is a mono- or dimethylbenzyl group, X is a lower alkoxycarbonyl group.

2. The method of protecting plants against agricultural or horticultural fungi as recited in claim 1, wherein R of formula (I) is a $C_1$–$C_{12}$-alkyl group.

3. The method of protecting plants against agricultural or horticultural fungi as recited in claim 2, wherein R of formula (I) is a $C_4$–$C_8$-alkyl group.

4. The method of protecting plants against agricultural or horticultural fungi as recited in claim 1, wherein in formula (I), X is a hydrogen atom or a halogen atom and Y is a lower alkyl group.

5. The method of protecting plants against agricultural or horticultural fungi as recited in claim 1, wherein in formula (I), X is a hydrogen atom or a chlorine atom, Y is a lower alkyl group and R is a $C_4$–$C_8$-alkyl group.

6. The method of protecting plants against agricultural or horticultural fungi as recited in claim 1, wherein in formula (I), X is a hydrogen atom, Y is methyl, and R is ethyl.

7. The method of protecting plants against agricultural or horticultural fungi as recited in claim 1, wherein in formula (I), X is a hydrogen atom, Y is methyl, and R is iso-propyl.

8. The method of protecting plants against agricultural or horticultural fungi as recited in claim 1, wherein in formula (I), X is a hydrogen atom, Y is methyl, and R is n-butyl.

9. The method of protecting plants against agricultural or horticultural fungi as recited in claim 1, wherein the formula (I), X is a hydrogen atom, Y is methyl, and R is n-pentyl.

10. The method of protecting plants against agricultural or horticultural fungi as recited in claim 1, wherein in formula (I), X is a hydrogen atom, Y is methyl, and R is n-hexyl.

11. The method of protecting plants against agricultural or horticultural fungi as recited in claim 1, wherein in formula (I), X is a hydrogen atom, Y is methyl, and R is benzyl.

12. The method of protecting plants against agricultural or horticultural fungi as recited in claim 1, wherein in formula (I), X is methyl, Y is methyl and R is benzyl.

13. The method of protecting plants against agricultural or horticultural fungi as recited in claim 1, wherein in formula (I), X is a hydrogen atom, Y is n-propyl, and R is n-hexyl.

14. The method of protecting plants against agricultural or horticultural fungi as recited in claim 1, wherein in formula (I), X is methyl, Y is methyl, and R is n-hexyl.

15. The method of protecting plants against agricultural or horticultural fungi as recited in claim 1, wherein in formula (I), X is chloro, Y is methyl, and R is n-butyl.

16. The method of protecting plants against agricultural or horticultural fungi as recited in claim 1, wherein in formula (I), X is chloro, Y is methyl, and R is n-hexyl.

17. The method of protecting plants against agricultural or horticultural fungi as recited in claim 1, wherein in formula (I), X is chloro, Y is methyl, and R is n-pentyl.

18. The method of protecting plants against agricultural or horticultural fungi as recited in claim 1, wherein in formula (I), X is chloro, Y is methyl, and R is iso-pentyl.

19. The method of protecting plants against agricultural or horticultural fungi as recited in claim 1, wherein in formula (I), X is fluoro, Y is methyl, and R is n-heptyl.

* * * * *

UNITED STATES PATENT AND TRADEMARK OFFICE
CERTIFICATE OF CORRECTION

PATENT NO. : 4,742,063
DATED : MAY 3, 1988
INVENTOR(S) : YUKIO TOKUNAGA ET AL

It is certified that error appears in the above-identified patent and that said Letters Patent is hereby corrected as shown below:

Column 10, line 40, change the formula

" 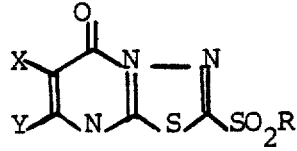 " to read,

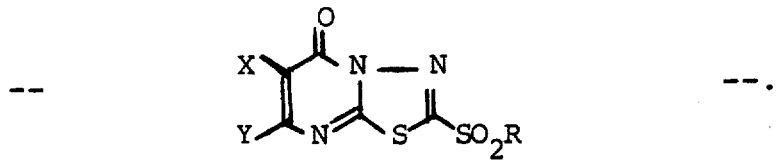 --.

Signed and Sealed this

Twenty-first Day of February, 1989

Attest:

DONALD J. QUIGG

Attesting Officer          Commissioner of Patents and Trademarks